United States Patent [19]
Suzuki

[11] Patent Number: 5,340,462
[45] Date of Patent: * Aug. 23, 1994

[54] AIR-FUEL RATIO SENSOR

[75] Inventor: Hiroyoshi Suzuki, Himeji, Japan

[73] Assignee: Mitsubishi Denki Kabushiki Kaisha, Tokyo, Japan

[*] Notice: The portion of the term of this patent subsequent to Dec. 22, 2009 has been disclaimed.

[21] Appl. No.: 74,295

[22] Filed: Jun. 9, 1993

[30] Foreign Application Priority Data

Jun. 25, 1992 [JP] Japan ................. 4-167354

[51] Int. Cl.$^5$ ............... G01N 27/26; F02D 41/14
[52] U.S. Cl. .................. 204/425; 204/426; 123/688; 123/697; 123/703
[58] Field of Search ........... 204/401, 406, 408, 424, 204/425, 426, 427; 123/697, 688, 703

[56] References Cited

U.S. PATENT DOCUMENTS

| | | | |
|---|---|---|---|
| 4,886,028 | 12/1989 | Uchinami et al. | 123/489 |
| 4,895,123 | 1/1990 | Uchinami et al. | 123/489 |
| 5,172,677 | 12/1992 | Suzuki | 123/697 |
| 5,172,678 | 12/1992 | Suzuki | 123/697 |

FOREIGN PATENT DOCUMENTS 241652 10/1986 Japan.
9357 1/1989 Japan.

Primary Examiner—John Niebling
Assistant Examiner—Bruce F. Bell
Attorney, Agent, or Firm—Sughrue, Mion, Zinn, Macpeak and Seas

[57] ABSTRACT

An air-fuel ratio sensor comprises an oxygen concentration cell device, an oxygen pump device, a heater for heating the oxygen concentration cell device and the oxygen pump device, a pump current cut means for stopping the supply of the pump current, first and second timers for controlling the condition of stopping the pump current, and a controller for starting the heating of the heater under the condition of stopping the pump current, to the pump device and for removing the stopping of the pump current for a predetermined time at predetermined intervals from the starting of supplying power to the heater, by means of the first timer, wherein when the pump current shows a predetermined value or higher, the pump current is stopped and the second timer is started, and when the operation of the second timer is finished, the judgment of the activation of the sensor is made, and at the same time, the stopping of the pump current is removed.

6 Claims, 15 Drawing Sheets

FIGURE 3(a) DRIVING HEATER

FIGURE 3(b) PUMP CURRENT CUT Tr

FIGURE 3(c) VOLTAGE OF CELL DEVICE

FIGURE 3(d) A/F RATIO OUTPUT

FIGURE 8(a) DRIVING HEATER

FIGURE 8(b) TEMPERATURE OF SENSOR DEVICE

FIGURE 8(c) ELECTROMOTIVE FORCE OF SENSOR

FIGURE 8(d) A/F RATIO OUTPUT

FIGURE 8(e) PUMP VOLTAGE OUTPUT

FIGURE 11(a) DRIVING HEATER

FIGURE 11(b) CONTROL CURRENT CUT Tr

FIGURE 11(c) VOLTAGE OF CELL DEVICE

FIGURE 11(d) A/F RATIO OUTPUT

FIGURE 13(a) DRIVING HEATER

FIGURE 13(b) CONTROL CURRENT CUT Tr

FIGURE 13(c) VOLTAGE OF CELL DEVICE

FIGURE 13(d) A/F RATIO OUTPUT

AIR-FUEL RATIO SENSOR

BACKGROUND OF THE INVENTION

Field of the Invention

The present invention relates to an air-fuel ratio sensor for detecting an air-fuel ratio for an internal combustion engine.

Discussion of Background

Heretofore, there has been proposed to conduct a feedback control of a fuel supply quantity by providing a whole range air-fuel sensor in the exhaust system of an internal combustion engine to thereby detect an exhaust air component related to an air-fuel ratio, so that the air-fuel ratio of an air-fuel mixture for the engine can be controlled to have a target value with accuracy over the entire region of the air-fuel ratio used. The air-fuel ratio sensor used for the conventional technique functioned only when the temperature of the sensor element portion became about 400° C. to 500° C. or higher. Accordingly, a heater for heating the sensor element portion was provided wherein the sensor element portion was determined to operate at an activating temperature or higher. However, when the engine was started from a state that the temperature of the sensor was low, there was a possibility of causing a failure in the sensor unless the sensor was used under confirmation that the temperature of the sensor element portion after the activation of the heater reached the activation temperature or higher.

There has been various proposals concerning the judgment that the air-fuel ratio sensor is in a state of activation. For instance, in Japanese Unexamined Patent Publication No. 241652/1986, the completion of the activation of the sensor is assumed when a predetermined time has passed after the initiation of heating the sensor by means of a heater. Further, in Japanese Unexamined Patent Publication No. 9357/1989, the activation state is assumed when a voltage across electrodes of a cell device and a pump element becomes in a predetermined range under a condition that an electric current is supplied to the pump element of the sensor.

A conventional air-fuel sensor will be described with reference to drawings.

FIG. 6 is a diagram showing a conventional engine control system wherein an air-fuel ratio control is conducted by using an air-fuel ratio sensor. In FIG. 6, reference numeral 1 designates an air-fuel sensor attached to the exhaust pipe 31 of an engine 30, numeral 2 designates a control amplifier in the air-fuel ratio sensor, numeral 3 designates an engine revolution sensor, numeral 4 designates an intake air quantity sensor, numeral 5 designates a cooling water temperature sensor disposed in the engine 30, numeral 6 designates an injector, numeral 7 designates an air-fuel ratio control section, numeral 8 designates a throttle valve, numeral 9 designates a throttle position sensor, and numeral 32 designates an intake air pipe. The sensors 3 to 5 and 9 respectively detect an engine revolution speed $N_e$, an intake air quantity $Q_a$, a cooling water temperature WT and a throttle position $\theta$, and values detected by the sensors are supplied to the air-fuel ratio control section 7. Air introduced into the intake air pipe 32 through the throttle valve 8 and the air-fuel ratio of a mixture of the air and fuel injected through the injector 6 is detected by the air-fuel ratio sensor 1, and the detected information is amplified by the control amplifier 2 to be supplied to the air-fuel ratio control section 7.

FIG. 7 is a diagram showing in detail the air-fuel ratio sensor 1, the control amplifier 2 and the air-fuel ratio control section 7. The air-fuel ratio sensor 1 comprises a sensor device 11 and a heater 12. The sensor device 11 comprises an oxygen pump device 11a, an oxygen concentration cell device 11b, a diffusion chamber 11c and an atmospheric chamber 11d. The oxygen pump device 11a and the oxygen concentration cell device 11b are formed of an oxygen ion conducting solid electrolyte each provided with an electrode, and they are disposed interposing therebetween the diffusion chamber 11c into which exhaust gas from the engine is introduced in a diffused state.

The heater 12 is for heating and activating the sensor device 11. The control amplifier 2 comprises a differential type integrating amplifier 21 as a pump current control means, a differential amplifier 22 as a pump current detecting means, a first non-inverse amplifier 23, a second non-inverse amplifier 33 as a pump voltage detecting means, and a heater control circuit 25.

In operation of the control amplifier 2, a voltage $V_S$ of the oxygen concentration cell device 11b is inputted to an inverse input terminal of the differential type integrating amplifier 21, and a reference voltage $V_{ref}$ is inputted to a non-inverse input terminal of the amplifier. An output from the differential type integrating amplifier 21 is inputted to the oxygen pump device 11a through a current detection resistor $R_S$. A voltage appearing at both ends of the current detection resistor $V_S$ is applied to the differential amplifier 22. An output from the differential amplifier 22 is inputted to a non-inverse input terminal of the non-inverse amplifier 23, while an off-set voltage $V_B$ is applied to an inverse input terminal of the non-inverse amplifier 23. Further, a voltage to be applied to the oxygen pump device 11a is applied to a non-inverse input terminal of a non-inverse amplifier 33, while an off-set voltage $V_{PB}$ is applied to an inverse input terminal of the amplifier 33.

The air-fuel ratio control section 7 comprises multiplexers 71a, 71b, A/D converters 72a, 72b, an input interface 73, a microprocessor 74, a ROM 75, a RAM 76, output interfaces 77a, 77b and an injector driving circuit 78. To the microprocessor 74, an output $N_e$ from the engine revolution sensor 3 is inputted through the input interface 73, an output $Q_a$ from the intake air quantity sensor 4 is inputted through the multiplexer 71a, an output WT from the cooling water temperature sensor 5 is inputted through the multiplexer 71a and the A/D converter 72a, an output $V_O$ from the non-inverse amplifier 23 is inputted through the multiplexer 71b, an output $V_{PO}$ from the non-inverse amplifier 33 is inputted through the multiplexer 71b and the A/D converter 72b respectively. On the other hand, the injector 6 is connected to the injector driving circuit 78, which is controlled by the microprocessor 74 through the output interface 77a. The heater control circuit 25 is controlled by the microprocessor 74 through the output interface 77b.

The operation of the conventional air-fuel ratio sensor will be described with reference to the diagram of FIG. 7 and a time chart in FIG. 8.

On starting the engine, the heater 12 of the air-fuel ratio sensor 1 is actuated and controlled by the heater control circuit 25. When the sensor device 11 is heated and activated, an inter-electrode voltage of the oxygen concentration cell device 11b, produces an electromotive force $V_S$ which corresponds to a difference in oxygen concentration between the diffusion chamber 11c and the atmospheric chamber 11d. When a pump current $I_P$ is supplied to the oxygen pump device 11a so that the electromotive force $V_S$ of the sensor device corresponds to a predetermined reference voltage $V_{ref}$ by means of the differential type integrating amplifier 21, the current $I_P$ is in proportion to the air-fuel ratio. The current $I_P$ is detected by the detection resistor $R_S$, and the detected value is amplified by the differential amplifier 22, and the amplified component is added with an off-set voltage $V_B$ in the non-inverse amplifier 23, whereby an air-fuel output $V_O$ is obtainable. The off-set voltage $V_B$ is so determined that the air-fuel output $V_O$ is a positive output irrespective of the direction of flowing the pump current $I_P$ because the direction of the pump current $I_P$ is different between a rich region and a lean region of the air-fuel ratio.

The air-fuel ratio control section 7 receives data of the engine revolution speed $N_e$, the intake air quantity $Q_a$, the throttle position $\theta$, the cooling water temperature WT and so on and calculates a target air-fuel ratio by means of the microprocessor 74 on the basis of the data and a program previously stored in the ROM 75. Further, the control section 7 corrects a time for opening the valve of the injector 6 on the basis of the target air-fuel ratio which is obtained from an output $V_O$ of air-fuel ratio obtained by measuring, and operates for a feedback control of the air-fuel ratio to the engine 30 for a target air-fuel ratio by injecting fuel in a time of opening of the valve of the injector 6.

The RAM 76 temporarily stores the data processed by the control section 7.

Description will be made as to a time chart at the actuation of the air-fuel ratio sensor 1 in FIG. 8 wherein the air-fuel ratio after the starting of the engine is in a rich state.

On starting the engine 30, the heater 12 starts heating by an instruction from the microprocessor 74 through the output interface 77b to the heater control circuit 25.

In the heating operation, when the temperature $T_S$ of the sensor device 11 is about 400° C. or lower, the electromotive force $V_S$ of the oxygen concentration cell device 11b, is remained low. Accordingly, an input of the differential type integrating amplifier 21 is large, and accordingly, a large pump voltage $V_P$ is applied to the oxygen pump device 11a. A pump voltage output $V_{PO}$ appears as a positive output because the off-set voltage $V_{PB}$ is added to the pump voltage $V_P$ at the non-inverse amplifier 33. In this case, little pump current $I_P$ flows because the impedance of the oxygen pump device 11a is high whereby the air-fuel ratio output $V_O$ substantially corresponds to the off-set voltage $V_B$.

When the temperature $T_S$ of the sensor device 11 reaches about 400° C. to 500° C., the electromotive force $V_S$ of the oxygen concentration cell device 11b increases to about the reference voltage $V_{ref}$. At this moment, a constant control of $V_{ref}$ to the electromotive force $V_S$ of the sensor is established, and the pump voltage $V_P$ gradually converges so that oxygen is supplied to the diffusion chamber 11c, i.e. the pump voltage output $V_{PO}$ has a relation of $V_{PO} \leq V_{PB}$, and so that the pump current $I_P$ becomes a value indicating the air-fuel ratio in the instant situation. The convergence of the pump voltage $V_P$ and the pump current $I_P$ are finished when the temperature $T_S$ of the sensor device 11 reaches about 700° C.

In conventional techniques, the activation of the air-fuel ratio sensor is determined as follows. A time period is set in the estimation of a time in which the temperature $T_S$ reaches about 700° C., and the judgment of the activation is made when the time period by the timer has expired. In another technique, the judgment of the activation is made when the pump voltage output $V_{PO}$ is in a predetermined permissible voltage range, $V_{PB} \pm \Delta V_P$. In another technique, the judgment of the activation of the sensor is made by providing a detection means for detecting the electromotive force $V_S$ of the sensor and finding that an error $\Delta V_S$ between the electromotive force $V_S$ and the reference voltage $V_{ref}$ is within a predetermined range and the pump voltage output $V_{PO}$ is within a predetermined permissible voltage range, $V_{PB} \pm \Delta V_{PB}$. However, the conventional techniques of judging the activation of the sensor have disadvantages as follows.

In the case of judging the completion of the activation when a predetermined time has passed after the starting the heating operation by the heater 12, the sensor is sometimes not activated even though the time period determined by the timer has finished depending on the operation of the engine after the starting, whereby a correct judgment of the activation can not be obtained. Accordingly, it was necessary to determine a large safety factor for the time period even when a timer was used. This required a relatively long time period for determining the activation of the sensor.

In the case of determining the activation of the sensor when the inter-electrode voltage between the cell device 11b and the pump device 11a is in a predetermined range under the condition that an electric current is supplied to the oxygen pump device 11a, an additional detection circuit is needed to detect the inter-electrode voltage between the cell device 11b and the pump device 11a. The provision of the additional detection circuit makes the circuit large. Further, a large voltage is continuously applied to the pump device 11a while the temperature of the sensor device 11 is low, with the result that the sensor is deteriorated so that the durability of the sensor becomes poor. Further, since the temperature at which the activation of the sensor is determined is as low as about 400° C. to about 500° C., and the temperature of the sensor does not reach about 700° C. which is practically used, an error in an air-fuel ratio output is large because of temperature dependence of the sensor device 11.

SUMMARY OF THE INVENTION

It is an object of the present invention to provide an air-fuel ratio sensor which eliminates the necessity of adding a detection circuit for detecting a voltage for a cell device and a pump device, and which is capable of detecting an activation point of the sensor with high accuracy without causing the deterioration of the sensor, and of detecting abnormality in the sensor.

The foregoing and other objects of the present invention have been attained by providing an air-fuel ratio sensor which comprises an oxygen concentration cell device and an oxygen pump device which are disposed interposing therebetween a diffusion chamber into which exhaust gas from an engine is introduced, wherein the oxygen concentration cell device and oxygen pump device are arranged in an exhaust system for the engine and made of an oxygen ion conducting solid electrolyte each attached with an electrode; a heater for heating the oxygen concentration cell device and the oxygen pump device; a pump current control means for controlling a pump current flowing into the oxygen pump device so that the voltage of the oxygen concentration cell device becomes a predetermined value; a pump current detection means for detecting the pump current; a pump current cut means for stopping the supply of the pump current; a power supplying means for supplying power to the heater; first and second timer means for controlling the condition of stopping the pump current; and a control means for starting the supply of power from the power supplying means to the heater under the condition of stopping the pump current, and for removing the condition of the stopping of the pump current for a predetermined time at predetermined intervals from the starting of the supplying of power to the heater, by means of the first timer means.

Further in accordance with the present invention, there is provided an air-fuel ratio sensor which comprises an oxygen concentration cell device and an oxygen pump device which are disposed interposing therebetween a diffusion chamber into which exhaust gas from an engine is introduced, wherein the oxygen concentration cell device and oxygen pump device are arranged in an exhaust system for the engine and made of an oxygen ion conducting solid electrolyte each attached with an electrode; a heater for heating the oxygen concentration cell device and the oxygen pump device; a pump current control means for controlling a pump current flowing into the oxygen pump device so that the voltage of the oxygen concentration cell device becomes a predetermined value; a bidirectional voltage limiter means connected in parallel to the oxygen pump means; a control current detection means for detecting a control current flowing in the parallel circuit; a control current cut means for stopping the supply of the control current; a power supplying means for supplying power to the heater; first and second timer means for controlling the condition of stopping the control current; and a control means for starting the supply of power from the power supplying means to the heater under the condition of the stopping of the control current, and for removing the condition of the stopping of the control current for a predetermined time at predetermined intervals from the starting of the supplying of power to the heater, by means of the first timer means.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

Figure 1:
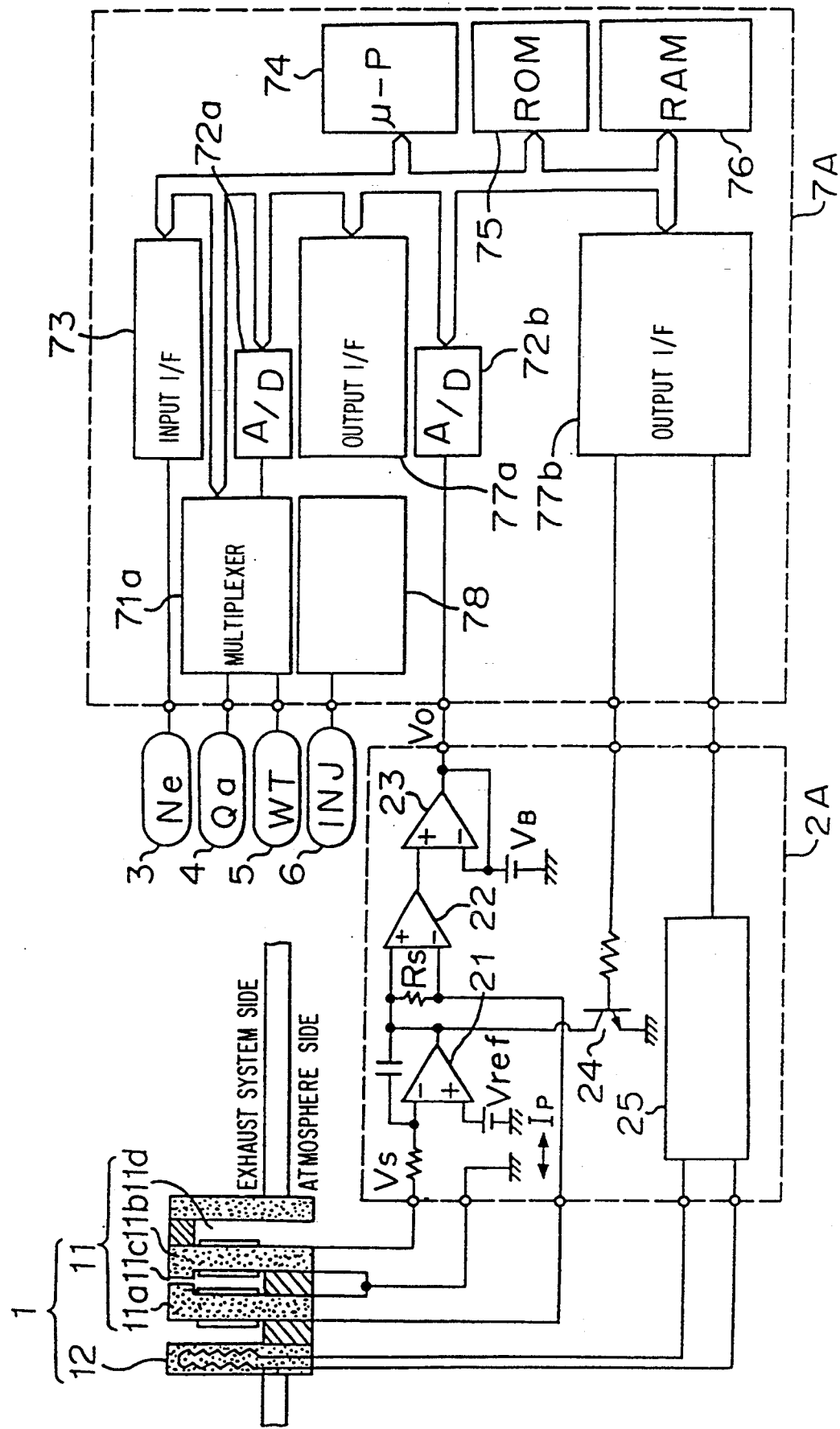
FIG. 1 is a diagram showing a first embodiment of the air-fuel sensor according to the present invention.
Figure 2:
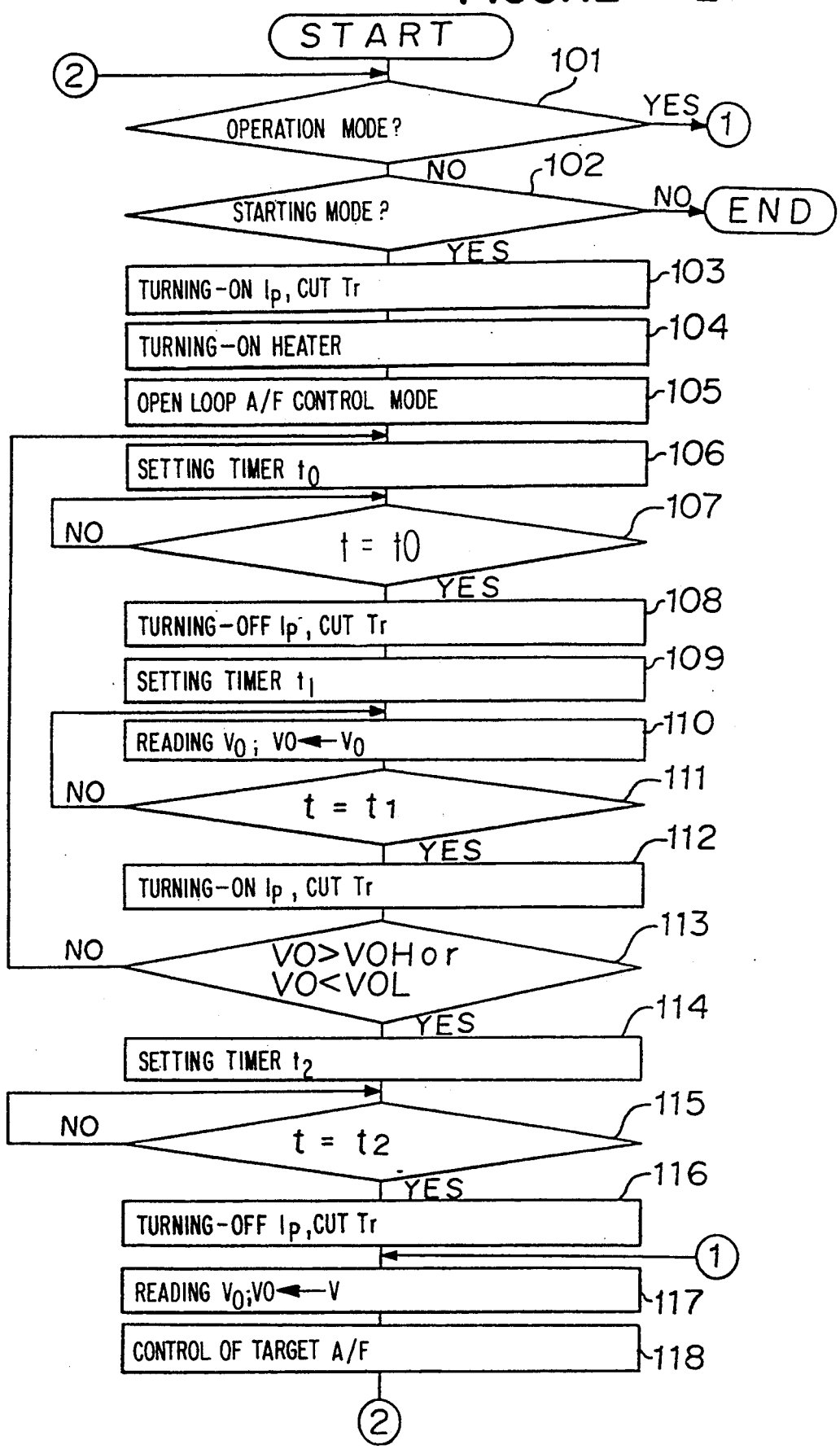
FIG. 2 is a flowchart showing the operation of the air-fuel ratio sensor of the first embodiment of the present invention.

Referring to the drawings wherein the same reference numerals designates the same or corresponding parts throughout the several views, and more particularly to FIG. 1 thereof, there is shown a diagram showing an air-fuel ratio sensor 1, a control amplifier 2A and an air-fuel ratio control section 7A in accordance with a first embodiment of the present invention; FIG. 2 of a flowchart showing an operation of determining the activation of the air-fuel ratio sensor 1, and FIG. 3 of a time chart showing the operation of determining the activation.

In FIG. 1, reference numeral 24 designates a pump current cut transistor which has a collector connected to an output terminal of a differential type integrating amplifier 21 and a base connected to an output interface 77b so that the transistor is turned-on and off depending on an output signal of the output interface 77b. In the first embodiment, a multiplexer 71b is not provided. The other structural elements are the same as those of the conventional air-fuel sensor.

The operation of the first embodiment will be described with reference to FIGS. 1, 2 and 3. When an engine 30 is started, data such as an engine revolution speed $N_e$, an intake air quantity $Q_a$ and so on are inputted to a microprocessor 74 in the air-fuel ratio control section 7A, and determination is made as to whether or not the engine 30 is operated regularly at Step 101 in FIG. 2. When the engine is not in regular operation, determination of a starting mode or not is made at Step 102. In this case, the determination of the starting mode is made when the engine revolution speed $N_e$ shows a predetermined value or lower.

Then, the pump current cut transistor 24 in the control amplifier 2A is turned on through the output interface 77b at Step 103. By turning-on the transistor 24, the output terminal of the differential type integrating amplifier 21 is grounded so that a pump current $I_p$ is not supplied to an oxygen pump device 11a.

A heater control circuit 25 is actuated through an output interface 77b at Step 104, in the same as Step 103. Then, power is supplied to a heater 12 so that a sensor device 11 is heated.

At Step 105, control of fuel at the starting time of the engine is conducted in an open-loop (O/L)A/F control mode.

Then, a timer is set to a time $t_0$ at Step 106. When the time $t_0$ in the timer is finished at Step 107, the pump current cut transistor 24 is turned-off at Step 108. Then, an output voltage of the differential type integrating amplifier 21 is applied to a pump device 11a so that the inter-electrode voltage of the cell device 11b becomes in correspondence to a reference voltage $V_{ref}$, whereby the pump current $I_P$ is supplied to the oxygen pump device 11a.

At Step 109, a timer is set to a time $t_1$ as soon as the pump current cut transistor 24 is turned off, and the supply of the pump current is continued during the operation of the timer having a time $t_1$. During the operation of the timer, the output of air-fuel ratio $V_O$ which corresponds to the pump current $I_P$ is A/D-converted by an A/D converter 72b and the A/D-converted datum is read by the microprocessor 74 at Step 110.

The operating time determined by the timer $t_1$ can be as small as about 100 msec or smaller, which depends on the response characteristic of the sensor and the PI constant of the differential time integrating amplifier 21, whereas the operating time of the timer $t_0$ is determined to be about 1 sec to about 2 sec.

When the operating time of the timer $t_1$ is finished at Step 111, the pump current cut transistor 24 is again turned on to thereby stop the supply of the pump current $I_P$ at Step 112.

At Step 113, determination is made as to whether or not the output of air-fuel ratio $V_O$ just before the finishing of the operating time of the timer $t_1$ reaches a predetermined value or higher, namely, determination is made as to whether or not the absolute value of the pump current $I_P$ is a predetermined value or more. When the output of air-fuel ratio $V_O$ does not reach the predetermined value, the operations of Step 106 through Step 113 are repeated.

On the other hand, when the output of air-fuel ratio $V_O$ reaches the predetermined value or higher, a timer having a time $t_2$ is set at Step 114. When the operation of the timer $t_2$ is finished at Step 115, the air-fuel ratio control section 7A judges that the sensor is activated, and the transistor 24 is turned-off to thereby supply the pump current $I_P$ at Step 116, whereby control is made to uniform the application of a voltage to the cell device 11b.

At Step 117, the value of the output of air-fuel ratio $V_O$ is read, and control of a target air-fuel ratio is conducted by using the air-fuel ratio output $V_O$ at Step 118.

Figure 3:
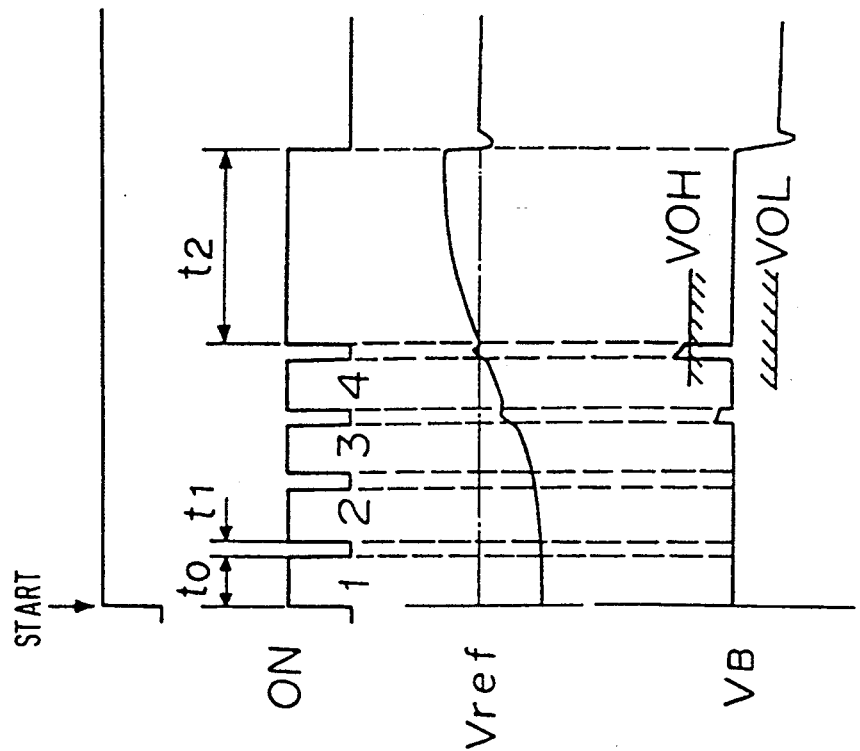
FIG. 3 is a time chart showing the operation of the air-fuel ratio sensor according to the first embodiment.

FIG. 3 is a time chart showing how to judge the activation of the air-fuel sensor at the time of starting of the engine wherein the air-fuel ratio at the starting is rich. FIG. 3a shows that the heater 12 is actuated on the starting of the engine 30. FIG. 3b shows that the pump current $I_P$ is supplied to the pump device 11a for a time period of $t_1$ at each interval of $t_0+t_1$. FIGS. 3c and 3d shows changes of the voltage $V_S$ of the cell device 11b under the condition of FIG. 3b and the air-fuel ratio output $V_O$, and determination levels $V_{OH}$ and $V_{OL}$ for the air-fuel ratio output $V_O$.

In FIG. 3, the temperature of the sensor is low in the first and second turns of time $t_1$ during which the pump current $I_P$ is supplied after the engine has been started. In this case, the electromotive force $V_S$ of the cell device 11b is small, and the internal resistance of the pump device 11a is too high to supply the pump current $I_P$. Accordingly, the air-fuel ratio output is remained as the off-set voltage $V_B$ (because $I_P=0$) although the output voltage of the differential type integrating amplifier 21 is large.

As the temperature of the sensor becomes high and the electromotive force $V_S$ of the cell device 11b increases, the internal resistance of the pump device 11a decreases whereby the pump current $I_P$ is supplied so as to feed oxygen. When the pump current $I_P$ is supplied, a voltage is applied to the pump device 11a by the differential type integrating amplifier 21 so as to feed oxygen from the diffusion chamber 11c to the pump device 11a with the result of increasing the voltage $V_S$ of the cell device 11b to the reference voltage $V_{ref}$, whereby the pump current $I_P$ is supplied. Accordingly, the air-fuel ratio output $V_O$ is gradually increased from the off-set voltage $V_B$.

FIG. 3d shows that the air-fuel ratio output $V_O$ exceeds a predetermined upper level of judgment $V_{OH}$ at the fourth turn of time $t_1$. The temperature of the sensor element 11 at this moment is about 500° C. or higher. The operation of stopping the pump current $I_P$ is continued until the temperature of the sensor becomes a stable condition, i.e. about 700° C. or higher which is a practically used temperature, by setting the timer having a time $t_2$.

In the first embodiment, when the temperature of the sensor device 11 is low, and control for making the voltage of the cell device 11b constant is not obtainable, the voltage is applied to the oxygen pump device 11a for only a short time which is determined by the timer $t_1$. Accordingly, there is no danger of causing the deterioration or breakage of the sensor due to the activation treatment. Further, the first embodiment described above allows the judgment of the activation without providing a detection circuit for detecting the voltage $V_S$ of the cell device 11b and the voltage $V_P$ of the pump device 11a.

In the first embodiment, the latest value of the air-fuel ratio output which has been measured in the operation of the timer $t_1$ is used in order to start the timer $t_2$. However, since the time period of the timer $t_1$ fixed, the air-fuel ratio output $V_O$ which has been measured only once just before the finishing of the operation of the timer $t_1$ may be used.

Further, in the first embodiment, description has been made as to a case that the time period of each of the timers $t_0$ and $t_2$ is fixed. However, the time period may be changed depending on an operational condition to obtain a faster judgment of the activation. Specifically, the time period may be determined as a reducing function for the cooling water temperature WT.

Figure 4:
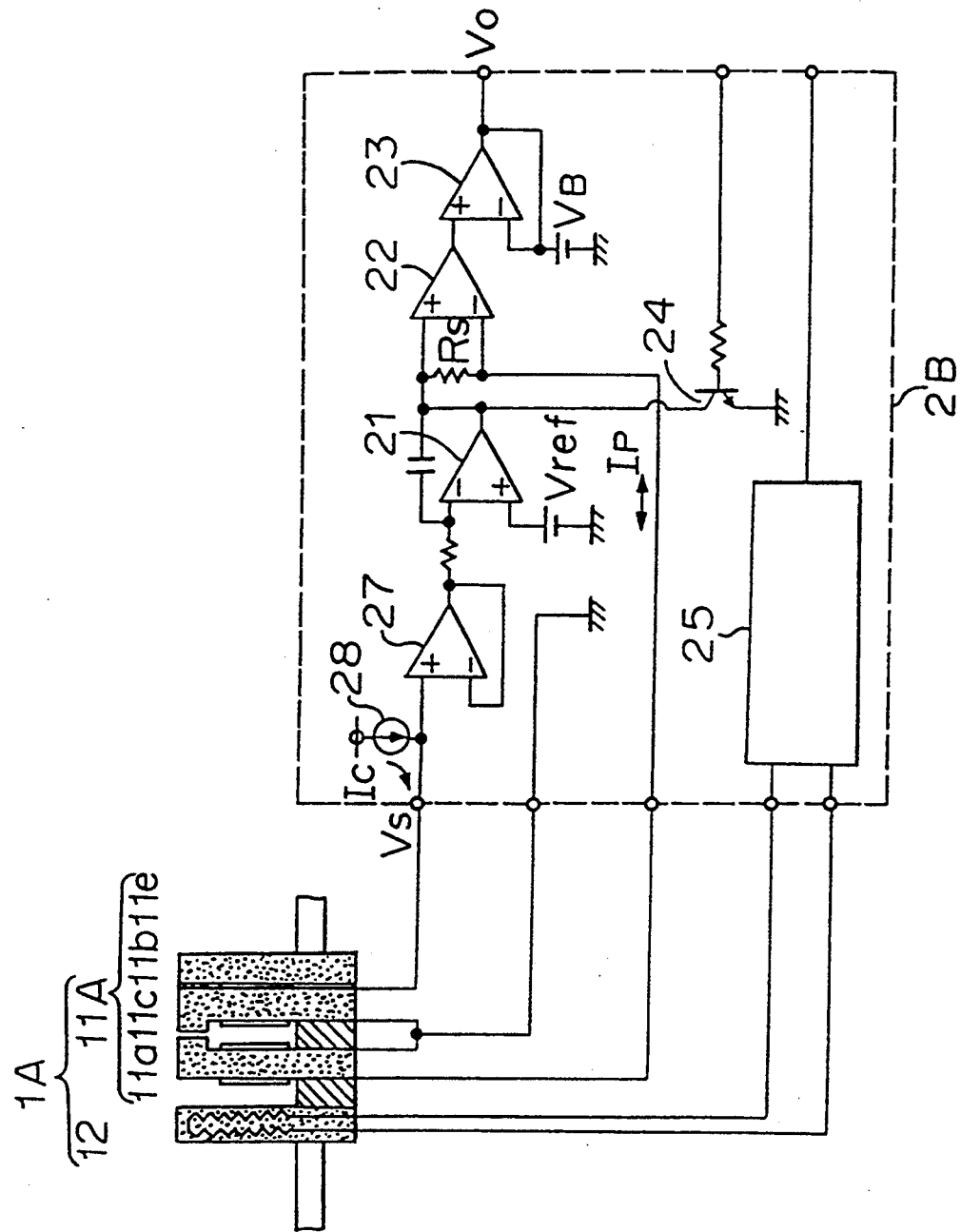
FIG. 4 is a diagram showing a second embodiment of the air-fuel sensor according to the present invention.

FIG. 4 is a diagram showing an air-fuel ratio sensor 1A and a control amplifier 2B according to a second embodiment of the present invention.

The air-fuel ratio sensor 1A comprises a sensor device 11A and the heater 2 which is used for the first embodiment. The sensor device 11A comprises an oxygen pump device 11a, an oxygen concentration cell device 11b, a diffusion chamber 11c and a reference electrode gap 11e. The reference electrode gap 11e faces an electrode which constitutes a pair of electrodes with another electrode attached to the side facing the diffusion chamber 11c of the cell device 11b.

The control amplifier 2B comprises a buffer 27 and a constant current source 28 which are not provided in the control amplifier 2A used for the first embodiment.

The buffer 27 has a non-inverse input terminal which is connected to the electrode at the side of the reference electrode gap 11e of the cell device 11b, and an output terminal connected to a differential type integrating amplifier 21. The constant current source 28 is connected to the electrode at the side of the reference electrode gap 11e of the cell device 11b.

The operation of the second embodiment of the present invention will be described with reference to a time chart shown in FIG. 5. The flow chart shown in FIG. 2 is also applicable to the second embodiment.

When the sensor device 11A is activated, an injection current $I_C$ of several tens μA flows from the constant current source 28 through the electrode disposed at the side of the reference electrode gap 11e of the cell device 11b to the electrode disposed at the side of the diffusion chamber 11e so that oxygen is supplied to the reference electrode gap 11e from the diffusion chamber 11c, whereby the partial pressure of oxygen can be kept at an order of several percents. Namely, the reference electrode gap 11e has the same function as the atmospheric chamber 11d in the first embodiment.

When the internal resistance of the cell device 11b is expressed by R, the electromotive force is E and a current supplied to the cell device is $I_C$, the voltage $V_S$ of the cell device 11b can be expressed as follow:

$$V_S + R \times I_C + E$$

Figure 5:
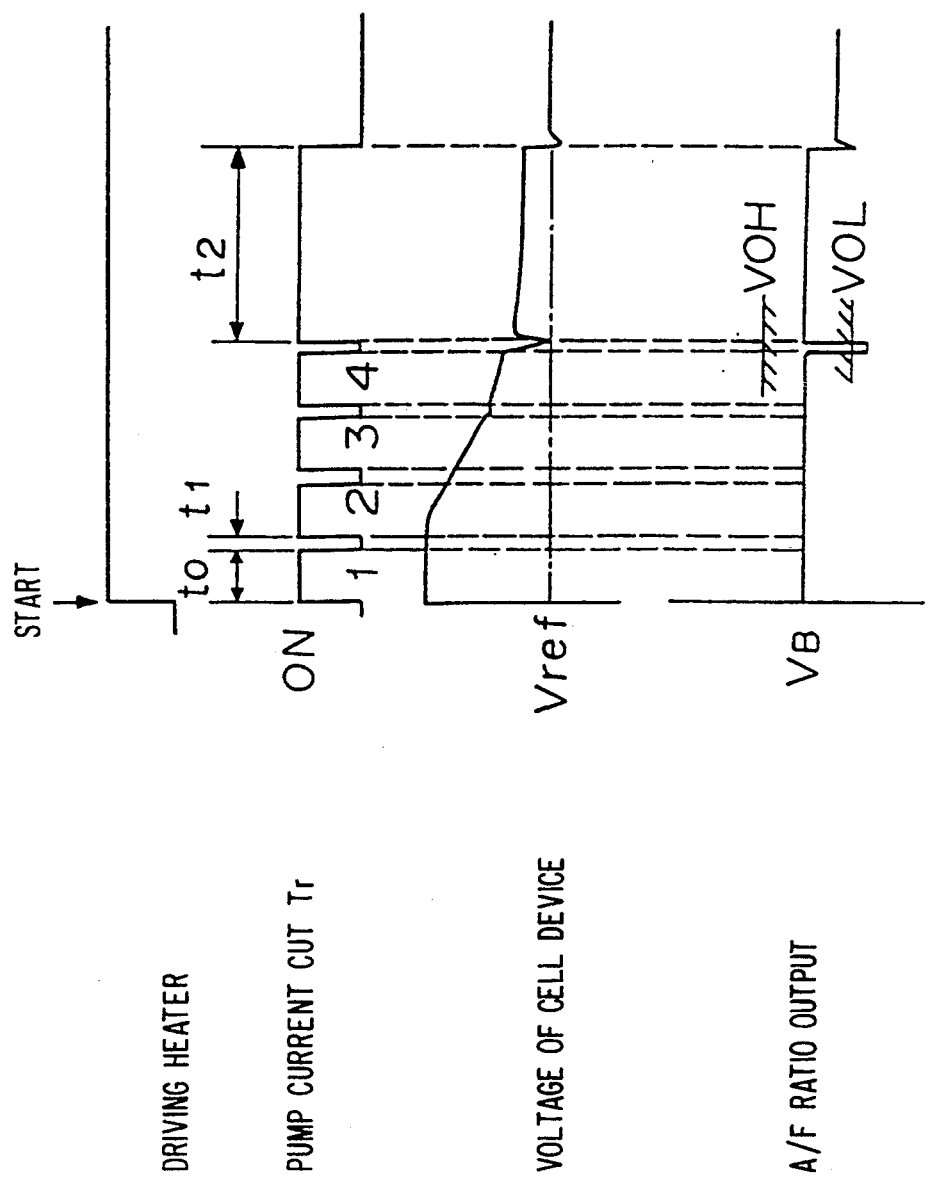
FIG. 5 is a time chart showing the operation of the air-fuel ratio sensor according to the second embodiment of the present invention.
Figure 6:
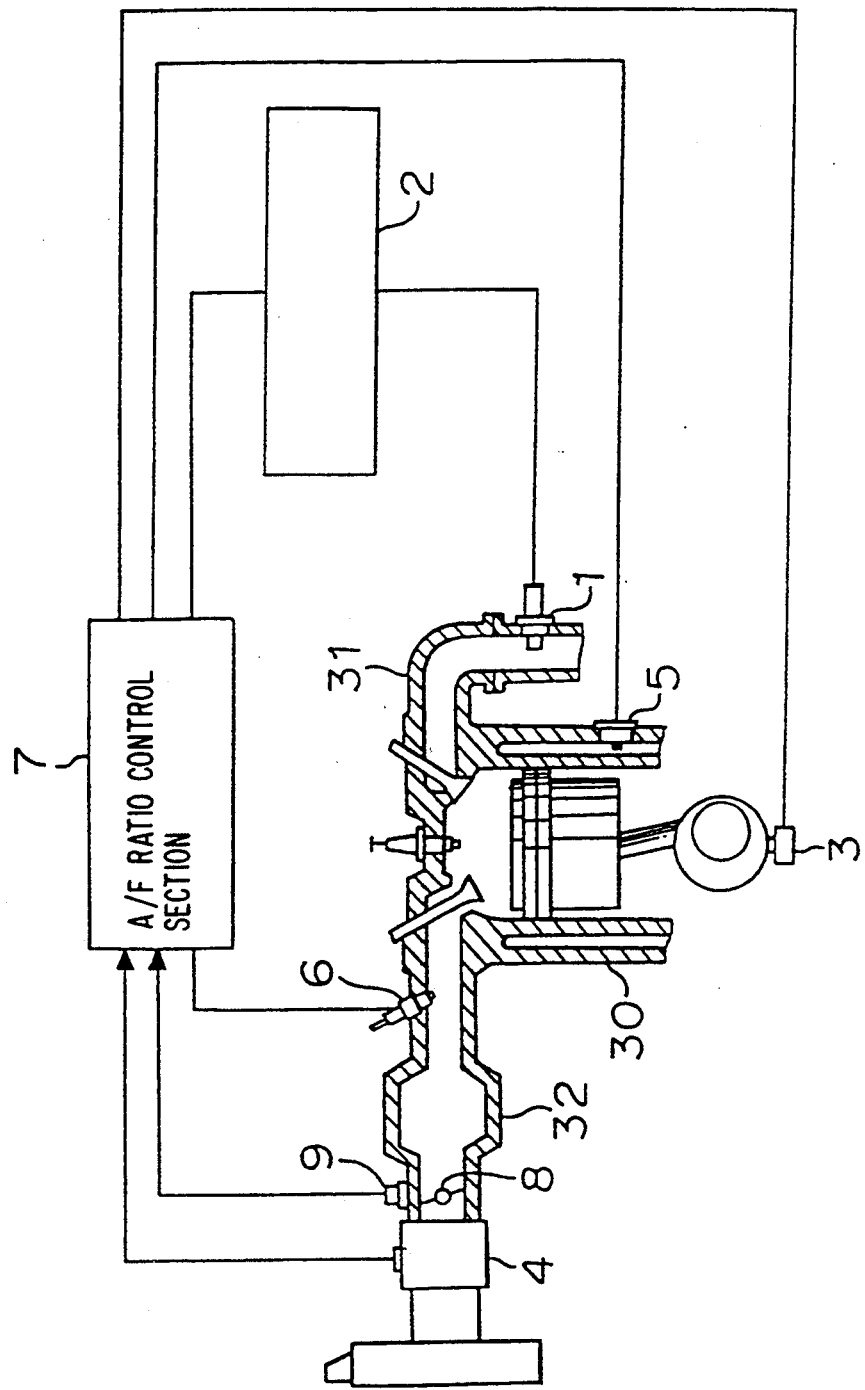
FIG. 6 is a diagram showing a conventional air-fuel ratio control device.
Figure 7:
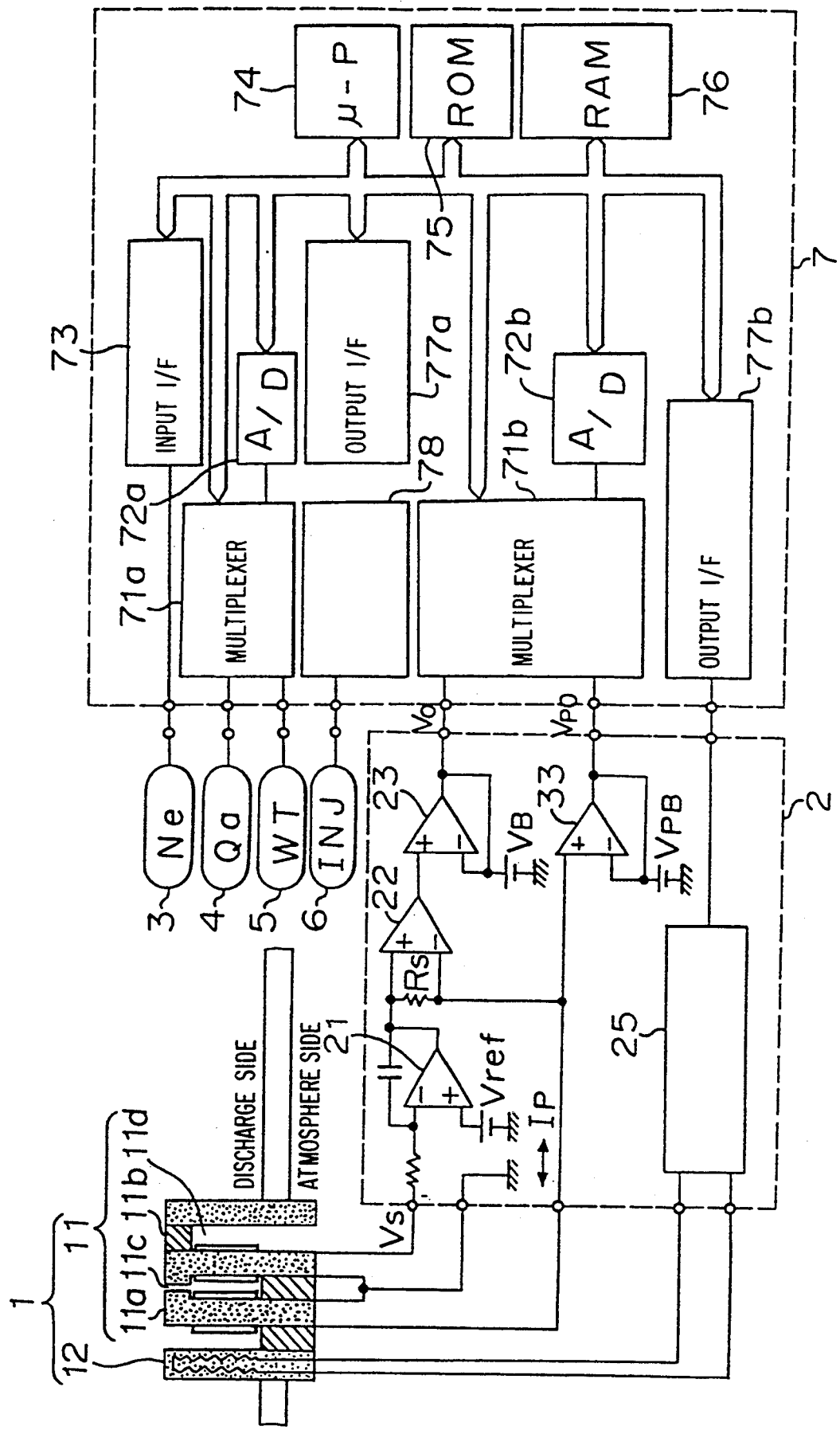
FIG. 7 is a diagram showing a conventional air-fuel ratio sensor.
Figure 8:
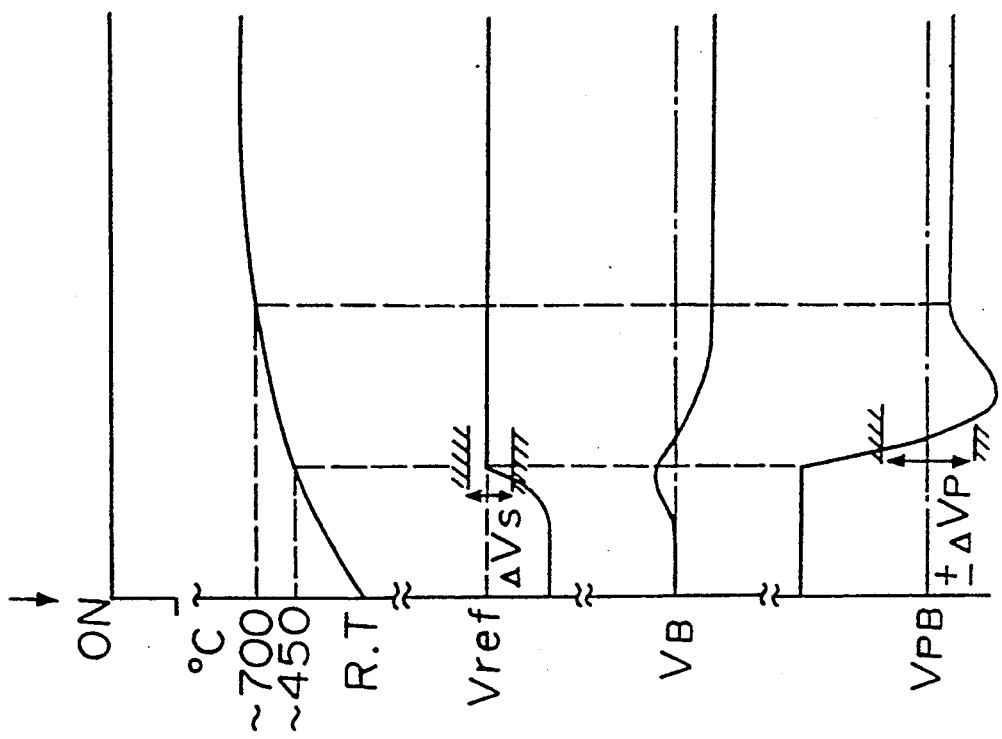
FIG. 8 is a time chart showing the operation of the conventional air-fuel ratio sensor.

In FIG. 5, a relation of $R \times I_C >> E$ is established until first and second turns of periods of time $t_1$ in which the temperature of the sensor is low. Accordingly, the voltage $V_S$ of the cell device 11b shows a value higher than $V_{ref}$ on the contrary to the first embodiment, and the direction of the output voltage of the differential type integrating amplifier 21 is opposite to that of the first embodiment. However, the pump current $I_P$ does not flow because the internal resistance of the pump device 11a is high in the same manner as the first embodiment. Accordingly, the air-fuel ratio output $V_O$ is remained as the off-set voltage $V_B$. When the temperature of the sensor device 11a is increased, the internal resistance R is decreased, and the electromotive force E is increased, the voltage $V_S$ is gradually reduced to be converged to an exhaust atmosphere. FIG. 5 shows that the air-fuel ratio is in a rich state, and a value of convergence is about 1 volt.

When the temperature of the sensor device becomes high, the voltage $V_S$ is decreased, the internal resistance of the pump device 11a is decreased, and the pump current $I_P$ is passed to carry oxygen, a voltage is applied to the pump device 11a by means of the differential type integrating amplifier 21 in a time of the supply of $I_P$ so that the voltage $V_S$ is reduced to the reference value $V_{ref}$, whereby the pump current $I_P$ is supplied in the direction to feed oxygen to the diffusion chamber 11c. Accordingly, the pump current $I_P$ is gradually increased in the direction opposite to the case described in the first embodiment. Namely, the air-fuel ratio output $V_O$ is gradually smaller than the off-set value $V_B$, the output $V_O$ becomes lower than an output judging value $V_{OL}$ at the fourth turn of time period $t_1$. Accordingly, the judgment of the activation can be conducted in the same manner as the first embodiment.

Figure 9:
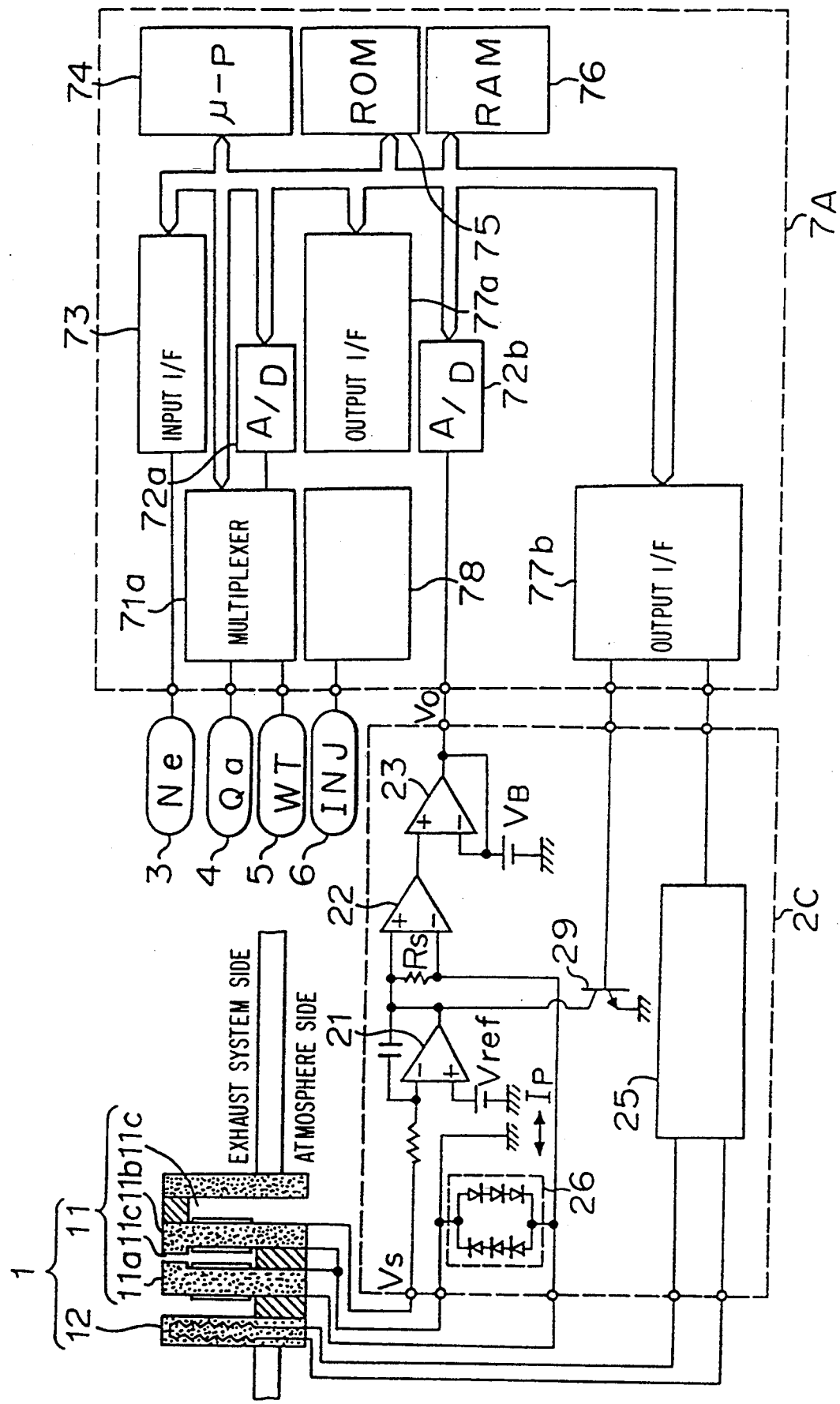
FIG. 9 is a diagram showing a third embodiment of the air-fuel ratio sensor according to the present invention.

FIG. 9 shows a diagram of an air-fuel ratio sensor 1, a control amplifier 2C and an air-fuel ratio control section 7A according to a third embodiment of the present invention.

In the third embodiment, the circuit of the control amplifier 2C is the same as that of the control amplifier 2A used for the first embodiment except that a bidirectional voltage limiter 26 is added, and a control current cut transistor 29 is used for the pump current cut transistor 24. The bidirectional voltage limiter 26 is connected in parallel to the oxygen pump device 11a, and is formed of a pair of three-serially-connected diodes.

In the third embodiment having the bidirectional voltage limiter 26, a range of voltage applied to the oxygen pump device 11a can be controlled within about ±1.8 volts. A control current $I_P$ flows in the parallel circuit.

Figure 10:
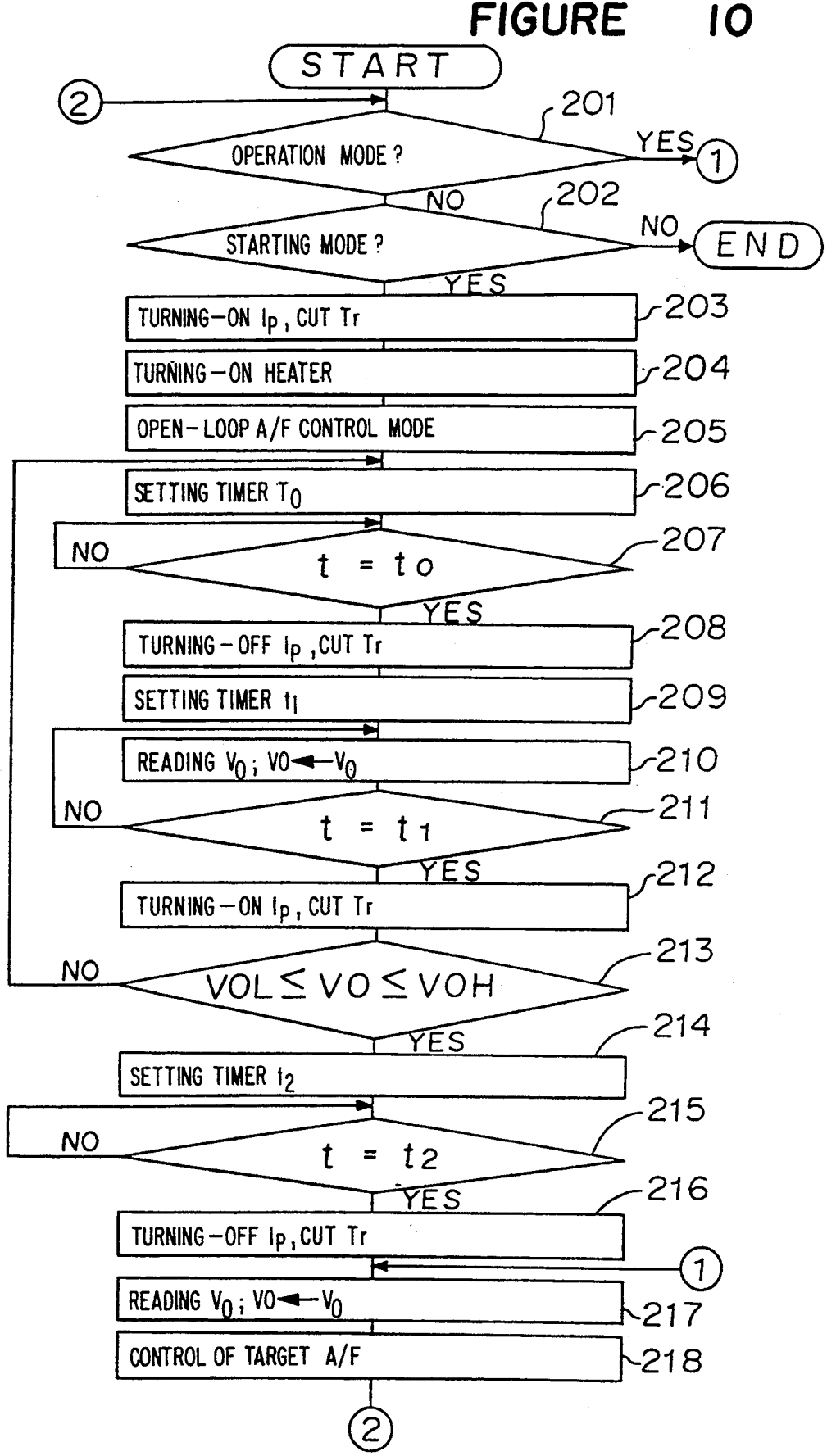
FIG. 10 is a flowchart showing the operation of the air-fuel ratio sensor according to the third embodiment of the present invention.

The operation of the third embodiment of the present invention will be described with reference to a flowchart in FIG. 10.

When an engine 30 is started, information such as an engine revolution speed $N_e$, an intake air quantity $Q_a$ and so on are supplied to a microprocessor 74. Then, determination is made as to whether or not the engine 30 is regularly operated at Step 201. When the engine is not regularly operated, determination is made as to whether or not the engine is in a starting mode at Step 202. The judgment of the starting mode is made when the engine revolution speed $N_e$ is a predetermined value or lower.

At Step 203, the control current cut transistor 29 is turned on through an output interface 77b whereby the output terminal of the differential type integrating amplifier 21 is grounded so as not to pass a control current to the pump device 11a.

At Step 204, a heater control circuit 25 is actuated to supply power to a heater 12. Then, the heating of a sensor device 11 is initiated. At Step 205, fuel control at the time of the starting of the engine is conducted.

At Step 206, a timer $t_0$ is set. When the operation of the timer $t_0$ is finished at Step 207, the control current cut transistor 29 is turned off at Step 208. Then, an output voltage of the differential type integrating amplifier 21 is applied to a parallel circuit consisting of the pump device 11a and the bidirectional voltage limiter 26 so that the inter-electrode voltage $V_S$ of the cell device 11b corresponds to a reference voltage $V_{ref}$, whereby a control current $I_P$ is passed. At Step 209, a timer $t_1$ is set. The releasing of the control current stopping operation by the transistor 29 is continued during the operation of the timer $t_1$.

At Step 210, the air-fuel ratio output $V_O$ corresponding to the control current $I_P$ is A/D-converted by an A/D converter 72b, and the converted value is read by the microprocessor 74.

In the same manner as the first embodiment, the operation of the timer $t_1$ can be short as about 100 msec or less while the operation of the timer $t_0$ is in a range of about 1 to 2 sec.

When the operation of the timer $t_1$ is finished at Step 211, the control current cut transistor 29 is again turned on at Step 212 to thereby stop the supply of the control current $I_P$.

At Step 213, determination is made as to whether or not the air-fuel ratio output $V_O$ just before the operation of the timer $t_1$ has finished is in a predetermined permissible range. When the air-fuel ratio output $V_O$ is out of the range, the operations of Steps 206 to 213 are repeated.

On the other hand, when the air-fuel ratio output $V_O$ is within the permissible range, a timer $t_2$ is set at Step 214.

When the operation of the timer $t_2$ is finished at Step 215, determination that the sensor device 11 has been activated is made. Then, the control current cut transistor 29 is turned off to thereby pass the control current $I_P$ at Step 216, and a constant voltage control is conducted to the cell device 11b.

At Step 217, the air-fuel ratio output $V_O$ is read, and a target air-fuel ratio control is conducted at Step 218.

Figure 11:
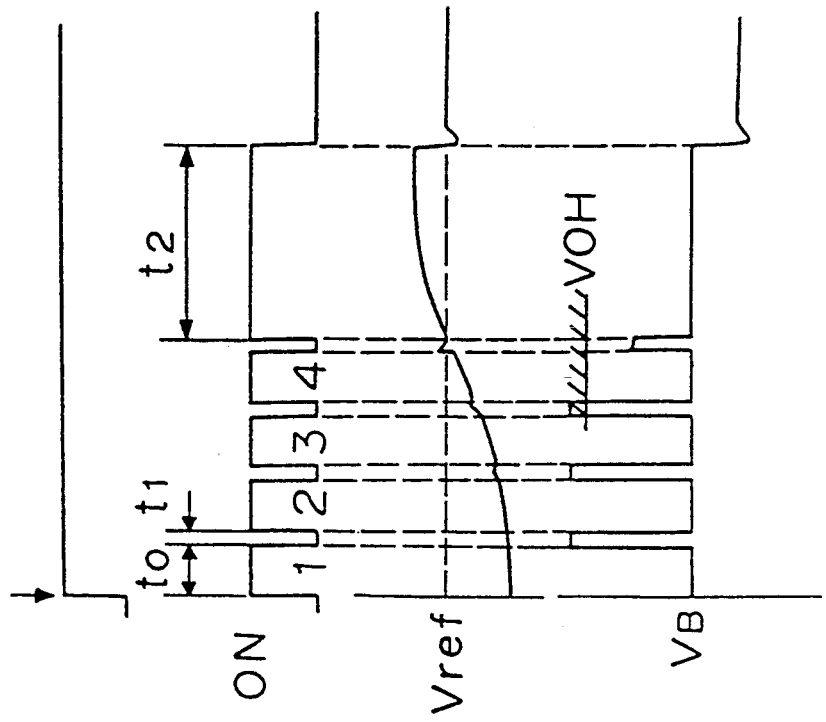
FIG. 11 is a time chart showing the operation of the third embodiment of the present invention.

FIG. 11 is a time chart for determining the activation of the sensor at the time of starting the engine wherein the air-fuel ratio at the starting time is rich.

FIG. 11a shows that the heater 12 is actuated upon the starting of the engine 30. FIG. 11b shows that the control current is passed for each period of time of $t_1$ at an interval of $t_0+t_1$. FIGS. 11c and 11d show changes of the voltage $V_S$ of the cell device and the air-fuel ratio output $V_O$, and a permissible range $V_{OH}$ of the air-fuel ratio output $V_O$ according to the operation of the control current cut transistor.

In FIG. 11, at the first and second turns of the time periods $t_1$ in which the control current $I_P$ is passed, the temperature of the sensor device 11 is low. Accordingly, the electromotive force $V_S$ of the cell device 11b is low and the internal resistance of the pump device 11a is high. In this state, no pump current flows, and accordingly, the control current of the differential type integrating amplifier 21 bypasses the bidirectional voltage limiter 26, whereby the voltage at both ends of the pump device 11a is maintained to be about 1.8 volts. Accordingly, the air-fuel ratio output $V_O$ shows a large value due to the bypass current.

As the temperature of the sensor element 11 is increased and the electromotive force $V_S$ of the cell device 11b is increased, the internal resistance of the pump device 11a is reduced to produce a pump current. When the pump current is passed to supply oxygen, a constant voltage control to the cell device 11b is established during the releasing of the control current stopping operation by the transistor 29. Then, the voltage at both ends of the pump device 11a becomes about 1.8 volts or lower. Then, the air-fuel ratio output $V_O$ is determined by the control current flowing in the pump device 11a.

FIG. 11 shows a case that the air-fuel ratio output $V_O$ becomes within the permissible range $V_{OH}$ at the fourth turn of the time period $t_1$. The temperature of the sensor in the state that the air-fuel ratio output $V_O$ is in the permissible range $V_{OH}$ is about 500° C. or higher. However, the supply of the control current $I_P$ is continued until the temperature reaches about 700° C. or higher, which is a practically used temperature range, by means of the timer $t_2$. The permissible range $V_{OH}$ can be determined in consideration of a range of the sensor output with respect to an air-fuel ratio used.

In the third embodiment, when the temperature of the sensor device 11 is low and a constant voltage control to the cell device 11b is not established, a voltage is applied to the oxygen pump device 11a for only a short time of the timer $t_1$. Accordingly, there is no danger of the deterioration or breakage of the sensor during the judgment of the activation of the sensor. Further, the judgment of the activation can be conducted without using a detection circuit to detect the voltage $V_S$ of the cell device 11b and the pump voltage $V_P$.

In the third embodiment, the operating time of the timer $t_0$ and $t_2$ is made constant. However, the operating time of the timers may be determined as reducing functions for the cooling water temperature WT so that the operating time is changed depending on operational conditions in order to obtain more rapid judgment of the activation.

Figure 12:
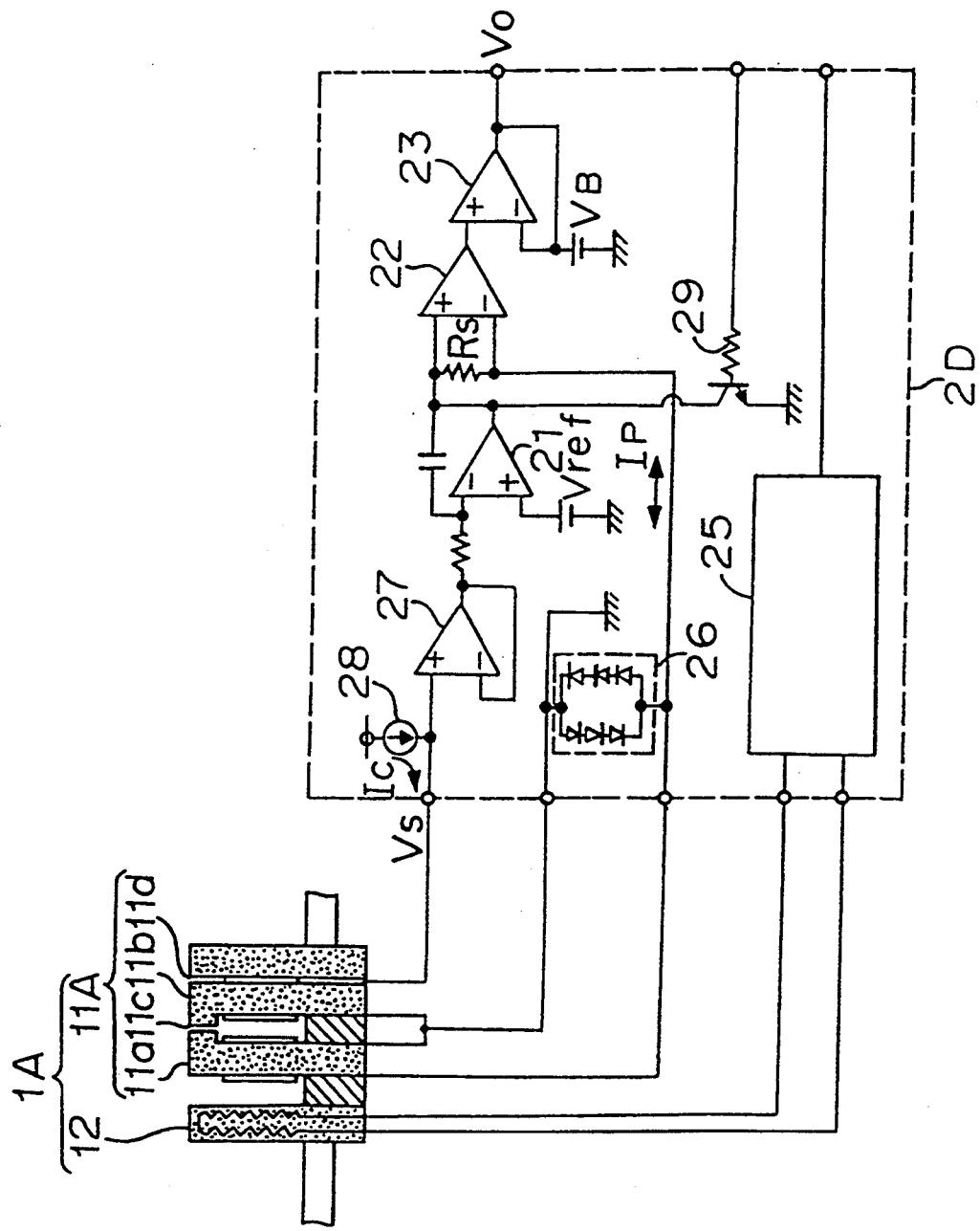
FIG. 12 is a diagram of a fourth embodiment of the air-fuel ratio sensor according to the present invention.

FIG. 12 is a diagram of an air-fuel sensor 1A and a control amplifier 2D according to a fourth embodiment of the present invention. The construction of the control amplifier 2D is the same as that of the control amplifier 2B used for the second embodiment except that a bidirectional voltage limiter 26 is incorporated. Further, a reference electrode gap 11e has the same function as an atmospheric chamber 11d.

The operation of the fourth embodiment of the present invention will be described with reference to a flow-chart in FIG. 10 and a time chart in FIG. 13.

In the first and second turns of operations of a timer $t_1$, the temperature of the sensor is low, and accordingly, there is a relation of $R \times I_C >> E$. Then, voltage $V_S$ of the cell device 11b shows a value higher than $V_{ref}$ which is contrary to the case of the third embodiment. A control current of a differential type integrating amplifier 21 flows in the direction opposite to the case of the third embodiment, and an air-fuel ratio output $V_O$ becomes a grounded state. When the temperature of the sensor is increased and the internal resistance R is reduced to thereby increase the electromotive force E, the voltage $V_S$ of the cell device 11b is gradually decreased, and the voltage $V_S$ is converged to a voltage in an atmosphere in the exhaust system.

Figure 13:
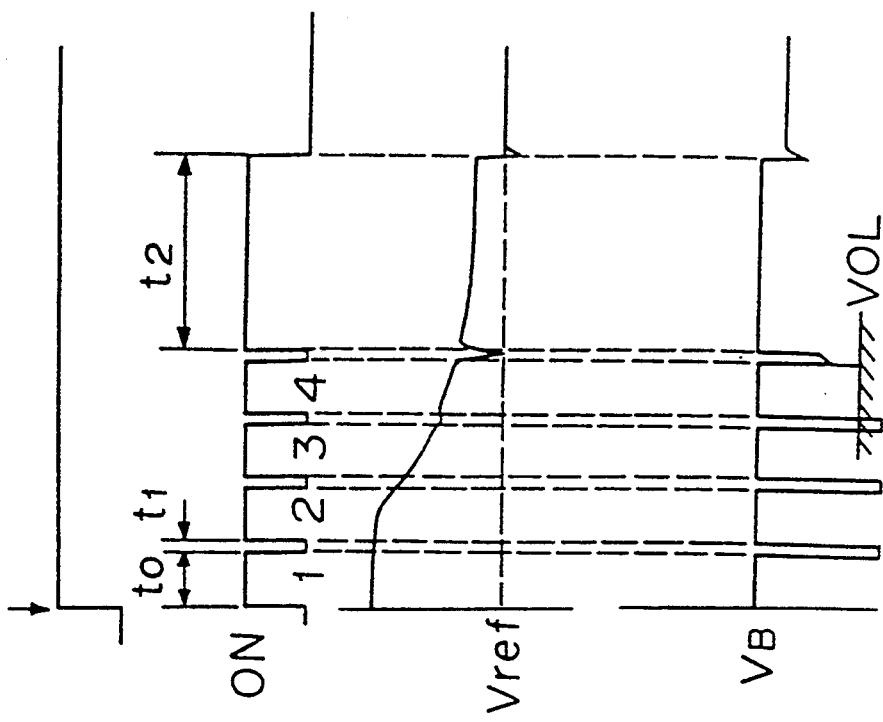
FIG. 13 is a time chart showing the operation of the fourth embodiment of the present invention.

FIG. 13 shows a case that the air-fuel ratio is rich, and a value of convergence is about 1 volt.

In the period of the fourth turns of the operation of the timer $t_1$, the control current stopping operation by control current cut transistor 29 is released under a condition that the temperature of the sensor device is increased. In this case, the pump device 11a supplies oxygen; a constant voltage control to a cell device 11b is established, and the air-fuel ratio $V_O$ assumes a value determined by the control current.

In the fourth embodiment, the air-fuel ratio output $V_O$ becomes within a permissible range $V_{OL}$. Thus, the judgment of the activation of the sensor can be conducted.

Figure 14:
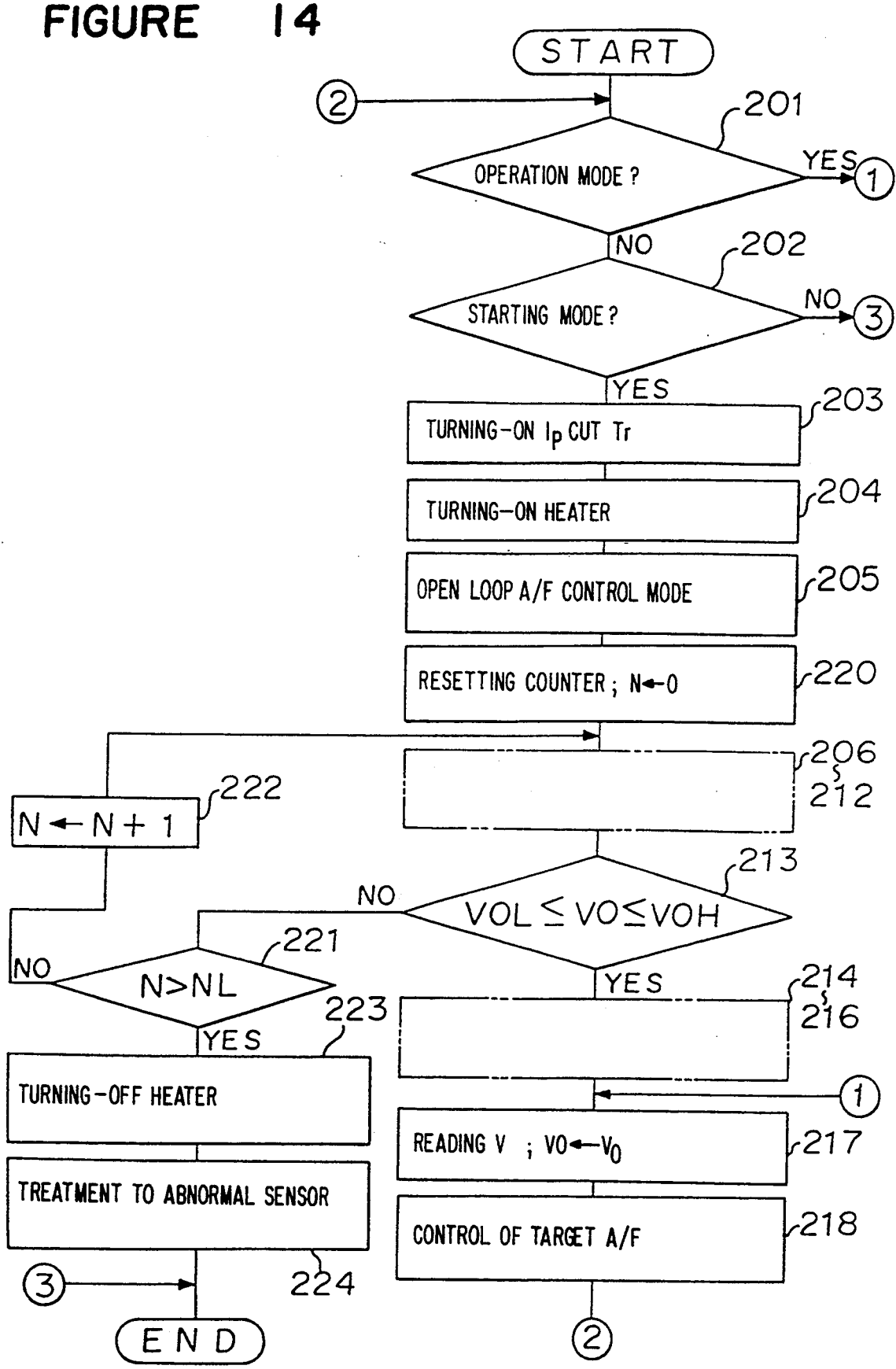
FIG. 14 is a flowchart showing the operation of an air-fuel ratio sensor according to a fifth embodiment of the present invention.

FIG. 14 is a flowchart showing the operation of a fifth embodiment of the present invention.

The operations of Step 201 to 218 are the same as those of the third embodiment.

At Step 220, a counter N is reset.

At Step 213, when a judgment that an air-fuel ratio output $V_O$ is out of a permissible range is made, determination is made as to whether or not a value of the counter N is a predetermined number NL or more at Step 221. When the value shows a lower value than NL, a value of +1 is added to the counter N at Step 222. Then, the operations of Step 206 to 213 are repeated.

When $N > NL$ at Step 221, a judgment that the sensor is abnormal is made. Then, power to be supplied to a heater 12 is stopped at Step 223, and a treatment of sensor abnormality is conducted at Step 224. For instance, when an accident of wire cut occurs in a pump device 11a, any control current is not supplied to the pump device 11a, and accordingly, a constant voltage control to a cell device 11b is not established, whereby a control current from a differential type integrating amplifier 21 is absorbed by bidirectional voltage limiter 26, and an air-fuel ratio output $V_O$ always exceeds a permissible range irrespective of the temperature of the sensor. In this case, a relation of N>NL is established at Step 221, namely, a judgment of sensor abnormality is made.

According to the fifth embodiment, a trouble concerning sensor abnormality such as wire-cutting in the heater 12 or the pump device 11a, abnormality in the electromotive force of the cell device 11b or the like can be detected even when a treatment of the activation judgment is conducted, without providing another detection circuit for detecting sensor abnormality. Further, a rapid judgment of abnormality can be conducted depending on the operating condition of the engine by changing a count value NL of the counter depending on the cooling water temperature WT.

Figure 15:
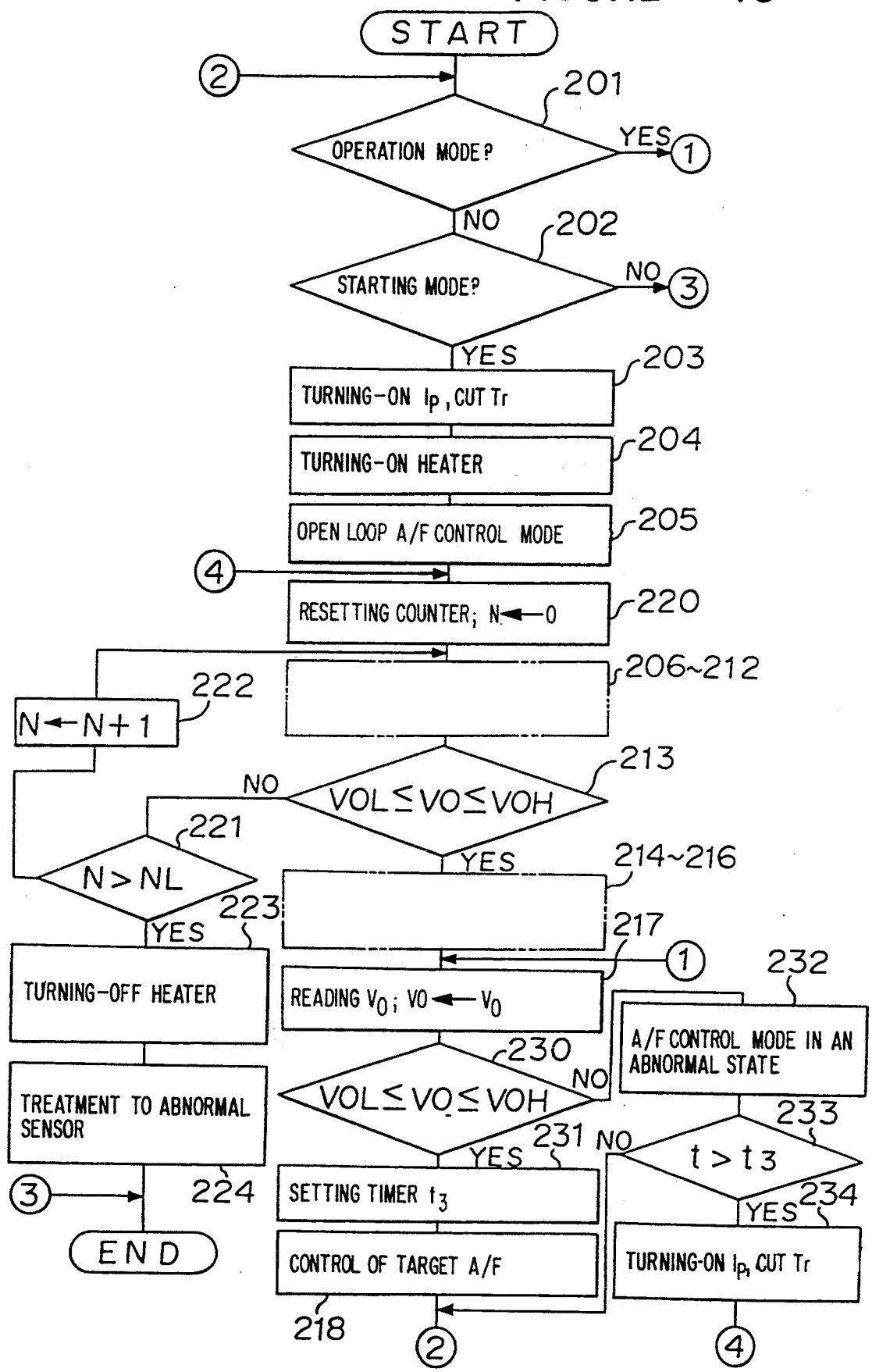
FIG. 15 is a flowchart showing the operation of the air-fuel ratio sensor according to a sixth embodiment of the present invention.

FIG. 15 is a flowchart showing the operation of the air-fuel ratio sensor according to a sixth embodiment of the present invention.

The operation of Steps 201 to 218 and 220 to 224 are the same as those of the fifth embodiment.

After the judgment of regular operation mode has been made at Step 201, an air-fuel ratio output $V_O$ is read at Step 217. Then, judgment is made as to whether or not the air-fuel ratio output $V_O$ is in a predetermined range at Step 230. When the air-fuel ratio output $V_O$ is in the predetermined range, a timer $t_3$ is set at Step 231.

At Step 218, control for target air-fuel ratio is conducted at Step 218, and operation is returned to Step 201.

When the air-fuel ratio output $V_O$ is out of the predetermined range at Step 230, an open-loop type air-fuel control mode in an abnormal state is taken without using the air-fuel ratio output $V_O$ at Step 232.

At Step 233, judgment is made as to whether or not the operation of the timer $t_3$ is finished. In a case of YES, namely, in a case that the air-fuel ratio output is beyond the permissible range during the regular operation of the engine for a predetermined time period, the control current is stopped at Step 234. Then, sequential operation is returned to Step 220 to conduct the judgment of the activation and the judgment of abnormality.

In accordance with the sixth embodiment, it is possible to make judgment as to whether abnormality is caused by the temporary inactivation due to reduction of the temperature of the sensor, or the sensor itself in a case that the abnormality is continuously caused in the air-fuel ratio output during the operation of the engine.

In the third to sixth embodiments, a pair of serially connected diodes are used as the bidirectional voltage limiter 26. However, another type voltage limiter circuit may be used.

In an aspect of the present invention, deterioration and breakage of sensor elements can be prevented since a pump current or a control current is not substantially passed during the treatment of judging the activation of the sensor. Further, since the judging of the activation can be conducted without detecting a voltage in the sensor device, a detection circuit can be eliminated. Further, a correct air-fuel ratio output can be obtained since an air-fuel ratio output is utilized after the temperature of the sensor device has been sufficiently elevated.

In another aspect of the present invention, a control current is supplied at a predetermined interval from the initiation of supplying power to a heater. Then, the judgment of sensor abnormality is made when the number of turns in the repeating operations of a first timer becomes a predetermined number of turns wherein the repeating operations are repeated when the control current is out of a predetermined range. According to this invention, an abnormal state of the sensor can be easily detected without adding a special circuit for detecting the abnormality.

In another aspect of the present invention, the judgment of the activation and the judgment of abnormality are simultaneously conducted when a control current is continuously out of a predetermined range for a predetermined time period. In accordance with this invention, it is possible to discriminate whether abnormality in the sensor output is caused by temporary inactivation due to reduction of the temperature or the sensor itself.

Obviously, numerous modifications and variations of the present invention are possible in light of the above teachings. It is therefore to be understood that within the scope of the appended claims, the invention may be practiced otherwise than as specifically described herein.

What is claimed is:

1. An air-fuel ratio sensor which comprises:
   an oxygen concentration cell device and an oxygen pump device which are disposed interposing therebetween a diffusion chamber into which exhaust gas from an engine is introduced, said oxygen concentration cell device and oxygen pump device being arranged in an exhaust system for the engine and made of an oxygen ion conducting solid electrolyte each attached with an electrode,
   a heater for heating the oxygen concentration cell device and the oxygen pump device,
   a pump current control means for controlling a pump current flowing into the oxygen pump device so that the voltage of the oxygen concentration cell device becomes a set value,
   a pump current detection means for detecting the pump current,
   a pump current cut means for stopping the supply of the pump current,
   a power supplying means for supplying power to the heater,
   first and second timer means for controlling the condition of stopping the pump current, and
   a control means for starting the supply of power from the power supplying means to the heater under the condition of stopping the pump current, and for removing the condition of the stopping of the pump current for a set time at predetermined intervals from the starting of the supplying of power to the heater, by means of the first timer means.

2. The air-fuel ratio sensor according to claim 1, wherein said control means stops the supply of the pump current by operating the second timer means when the pump current shows a set value or higher; judges that the oxygen concentration cell device and the oxygen pump device become activated when the operation of the second timer means has finished, and under the judgment, the condition of the stopping of the pump current is removed.

3. An air-fuel ratio sensor which comprises:
   an oxygen concentration cell device and an oxygen pump device which are disposed interposing therebetween a diffusion chamber into which exhaust gas from an engine is introduced, said oxygen concentration cell device and oxygen pump device being arranged in an exhaust system for the engine and made of an oxygen ion conducting solid electrolyte each attached with an electrode,
   a heater for heating the oxygen concentration cell device and the oxygen pump device, a pump current control means for controlling a pump current flowing into the oxygen pump device so that the voltage of the oxygen concentration cell device becomes a set value, a bidirectional voltage limiter means connected in parallel to the oxygen pump means, a control current detection means for detecting a control current flowing in the parallel circuit, a control current cut means for stopping the supply of the control current, a power supplying means for supplying power to the heater, first and second timer means for controlling the condition of stopping the control current, and a control means for starting the supply of power from the power supplying means to the heater under the condition of the stopping of the control current, and for removing the condition of the stopping of the control current for a set time at set intervals from the starting of the supplying of power to the heater, by means of the first timer means.

4. The air-fuel ratio sensor according to claim 3, wherein said control means stops the supply of the control current by operating the second timer means when the control current shows a set value or higher; judges that the oxygen concentration cell device and the oxygen pump device become activated when the operation of the second timer means has finished, and under the judgment, the condition of the stopping of the control current is removed.

5. The air-fuel ratio sensor according to claim 3, which further comprises an integrating means for integrating the number of repeating of the operation of the first timer means, and an abnormality judging means which makes the judgment of abnormality when the number of integration exceeds a set value and stops the supply of power to the heater.

6. The air-fuel ratio sensor according to claim 3, wherein the control means makes the judgment of the activation or abnormality when the control current is out of a set range for a set time period, during the operation of the engine.

* * * * *